United States Patent [19]

Hanes et al.

[11] 4,418,219

[45] Nov. 29, 1983

[54] PREPARATION OF METHYL TERTIARY-BUTYL ETHER

[75] Inventors: Ronnie M. Hanes, Milford; Orville D. Prampton, Wyoming, both of Ohio

[73] Assignee: National Distillers and Chemical Corporation, New York, N.Y.

[21] Appl. No.: 360,531

[22] Filed: Mar. 22, 1982

Related U.S. Application Data

[63] Continuation of Ser. No. 239,249, Mar. 2, 1981, abandoned.

[51] Int. Cl.$^3$ .............................................. C07C 41/06
[52] U.S. Cl. .................................................. 568/697
[58] Field of Search ................................ 568/697, 401

[56] References Cited

U.S. PATENT DOCUMENTS

| | | |
|---|---|---|
| 1,873,536 | 8/1932 | Brown et al. . |
| 2,536,768 | 1/1951 | Reynolds et al. . |
| 2,683,753 | 7/1954 | Levy et al. . |
| 2,694,049 | 11/1954 | Reynolds et al. . |
| 2,805,260 | 9/1957 | Keith . |
| 3,728,408 | 4/1973 | Tobias . |
| 3,758,615 | 9/1973 | Izumi et al. ........................ 568/901 |
| 3,966,586 | 6/1976 | Owen et al. . |
| 4,096,194 | 6/1978 | Moy . |
| 4,262,145 | 4/1981 | Selwitz et al. . |

FOREIGN PATENT DOCUMENTS 133661  1/1979  Fed. Rep. of Germany .

OTHER PUBLICATIONS

Venuto, Chem. Tech. Apr. 1971, 215–224.
Millor, Compehensive Treatise on Inorganic & Theoretical Chemistry, Longmans, Green & Co., New York, vol. XI, 747, (1948).
Hougen, Reeves & Mannella, I & E. C. 48, No. 2, (1956), p. 319.

*Primary Examiner*—Howard T. Mars
*Attorney, Agent, or Firm*—Kenneth D. Tremain

[57] ABSTRACT

Methyl tertiary-butyl ether (MTBE), a high-octane blending agent for motor fuels, is prepared in high yield by the process which comprises reacting isobutylene and methanol in the presence of a catalytically effective amount of at least one heterogeneous catalyst selected from the group consisting of boron phosphate, blue tungsten oxide and crystalline aluminosilicate zeolite having a silica to alumina mole ratio of at least about 12:1 and a constraint index of from 1 to about 12.

12 Claims, No Drawings

PREPARATION OF METHYL TERTIARY-BUTYL ETHER

This is a continuation of application Ser. No. 239,249, filed Mar. 2, 1981 now abandoned.

BACKGROUND OF THE INVENTION

1. Field of the Invention

This invention relates to the preparation of ethers and, more particularly, to the preparation of methyl tertiary-butyl ether.

2. Description of the Prior Art

Methyl tertiary-butyl ether (MTBE) is a high-octane blending agent for motor fuels and can have a blending Research Octane Number (RON) of over 120 in lead-free gasoline. The considerable interest taken in MTBE and processes for its economical large scale manufacture is evident in the many patent and literature references which relate to this compound (see, for example, U.S. Pat. Nos. 1,968,601; 2,067,385; 2,197,023; 2,282,469; 2,391,084; 2,480,940; 2,544,392; 2,805,260; 2,853,331; 3,135,807; 3,718,701; 3,726,942; 3,821,315; 3,825,603; 3,846,088; 3,849,082; and, 4,148,695; Belgian Pat. Nos. 612,388; 829,299; 829,300; and 829,303; British Pat. No. 1,272,585; and, German Pat. Nos. 2,246,004 and 2,521,963 among others). Many proposals for making MTBE are based on the catalyzed reaction of isobutylene with methanol. According to U.S. Pat. No. 2,805,260, this reaction can be catalyzed by boric acid and inorganic complexes of heteropoly acids. In U.S. Pat. No. 3,135,807, the catalyst of choice is bismuth molybdate or a lead, antimony, tin, iron, cerium, bismuth, nickel, cobalt or thorium salt of phosphomolybdic acid optionally supported on an inert carrier. U.S. Pat. No. 3,821,315 discloses still other molybdenum-containing catalysts. One widely studied catalyst is based on a cation exchange resin such as divinyl benzene cross-linked polystyrene cation exchange resin in which the active sites are sulfuric acid groups (viz, U.S. Pat. Nos. 3,726,942; 3,821,315; 3,846,088; and 3,849,082; and, German Pat. Nos. 2,629,769; 2,646,333; and 2,752,111). Polish Pat. No. 103,379 discloses the preparation of MTBE from methanol and isobutylene over zeolite X or Y which was largely dealuminized and cation exchanged.

SUMMARY OF THE INVENTION

It has now been discovered that isobutylene and methanol can be very efficiently reacted to provide MTBE in high yield employing a solid, i.e., heterogeneous, inorganic catalyst selected from the group consisting of boron phosphate, blue tungsten oxide and crystalline aluminosilicate zeolite having a silica to alumina mole ratio of at least about 12 and a constraint index, as hereinafter defined, of from 1 to about 12.

Contrary to expectations and unlike most other acidic catalysts, the heterogeneous inorganic catalysts herein provide excellent selectivity for MTBE but with relatively little co-production of isobutylene dimers and trimers.

DESCRIPTION OF THE PREFERRED EMBODIMENTS

Useful boron phosphate catalysts can be prepared with a range of phosphorus to boron mole ratios. Boron phosphates having mole ratios of boron to phosphorus of from about 0.4 to about 1.4, and especially from about 0.5 to about 0.7, are preferred catalysts herein. The boron phosphates can be prepared by known methods, for example, the method described in Goltz, et al., *J. Catal.* 22, 85 (1971) which is incorporated by reference herein.

Blue tungsten oxide which is useful as a catalyst in the process of this invention is commonly prepared by the reduction of tungsten trioxide employing known procedures, usually with hydrogen gas as the reducing agent, to provide an oxide variously described as $W_4O_{11}$ and $W_2O_5$. Accordingly, both reduced tungsten oxides are included within the scope of this invention.

Boron phosphate and blue tungsten oxide can be employed as such or in combination with an inert inorganic support or carrier, e.g., zinc spinel, alumina, silica, magnesia, titania, silica-alumina, alumina-magnesia, zirconia, pumice, kieselguhr, clays, bauxite, charcoal, and the like. If supported, the catalytically active component should represent at least 5 weight percent of the total composition.

Briefly, the zeolites useful in this invention possess, in combination: a silica to alumina mole ratio of at least about 12:1; and a structure providing constrained access to the crystalline free space. The silica to alumina mole ratio referred to may be determined by conventional analysis. This ratio is meant to represent, as closely as possible, the ratio in the rigid anionic framework of the zeolite crystal and to exclude aluminum in the binder or in cationic or other form within the channels. Although zeolites with a silica to alumina mole ratio of at least 12 are useful, it is preferred to use zeolites having higher mole ratios, e.g., at least about 30:1 with mole ratios of 10,000:1 and even higher being entirely suitable.

The crystalline aluminosilicate zeolites to be useful as catalysts herein must also provide constrained access to some larger molecules. It is sometimes possible to judge from a known crystal structure whether such constrained access exists. For example, if the only pore windows in a crystal are formed by 8-membered rings of oxygen atoms, then access by molecules of larger cross-section than normal hexane is substantially excluded and the zeolite is not of the desired type. Zeolites with windows of 10-membered rings are preferred, although excessive puckering or pore blockage may render these zeolites substantially ineffective. Rather than attempt to judge from crystal structure whether or not a zeolite possesses the necessary constrained access, a simple determination of the "constraint index" may be made by continuously passing a mixture of equal weight of normal hexane and 3-methylpentane over a small sample, approximately 1 gram or less, of zeolite at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 1,000° F. for at least 15 minutes. The zeolite is then flushed with helium and the temperature adjusted between 550° F. and 950° F. to give an overall conversion between 10% and 60%. The mixture of hydrocarbons is passed at 1 liquid hourly space velocity (i.e., 1 volume of liquid hydrocarbon per volume of catalyst per hour) over the zeolite with a helium dilution to give a helium to total hydrocarbon mole ratio of 4:1. After 20 minutes on stream, a sample of the effluent is taken and analyzed, most conveniently by gas chromatography, to determine the fraction remaining unchanged for each of the two hydrocarbons.

The "constraint index" is calculated as follows:

$$\text{Constraint index} = \frac{\log_{10} \text{(fraction of n-hexane remaining)}}{\log_{10} \text{(fraction of 3-methylpentane remaining)}}$$

Catalysts suitable for the present invention are those which employ a zeolite having a constraint index of 12.0 or less. Constraint Index (C.I.) values for some typical zeolite within the scope of this invention are:

| Zeolite | C.I. |
| --- | --- |
| ZSM-5 | 8.3 |
| ZSM-11 | 8.7 |
| ZSM-35 | 6.0 |
| TMA Offretite | 3.7 |
| ZSM-38 | 2.0 |
| ZSM-12 | 2 |

The above described Constraint Index is an important, and even critical, definition of those zeolites which are useful to catalyze the instant process. The very nature of this parameter and the recited technique by which it is determined, however, admit of the possibility that a given zeolite can be tested under somewhat different conditions and thereby have different constraint indexes. Constraint Index seems to vary somewhat with severity of operation (conversion). Therefore, it will be appreciated that it may be possible to so select test conditions to establish multiple constraint indexes for a particular given zeolite which may be both inside and outside the above defined range of 12 and less. Thus, it should be understood that the parameter and property "Constraint Index" as such value is used herein is an inclusive rather than an exclusive value. That is, a zeolite when tested by any combination of conditions within the testing definition set forth herein above to have a constraint index of 12 and less is intended to be included in the instant catalyst definition regardless that the same identical zeolite tested under other defined conditions may give a constraint index value above 12.

The class of preferred zeolites herein is exemplified by ZSM-5, ZSM-11, ZSM-12, and other similar materials. U.S. Pat. No. 3,702,886 describing and claiming ZSM-5 is incorporated herein by reference. ZSM-11 is more particularly described in U.S. Pat. No. 3,709,979, the entire contents of which are incorporated herein by reference. ZSM-12 is more paticularly described in U.S. Pat. No. 3,832,449, the entire contents of which are incorporated herein by reference. ZSM-35 is described in U.S. Pat. No. 4,016,265 and ZSM-38 is described in U.S. Pat. No. 4,046,859, both of said patents being incorporated by reference herein.

The preferred crystalline aluminosilicates are ZSM-5, ZSM-11 and ZSM-12 with ZSM-5 being particularly preferred.

The zeolites used as catalysts in this invention may be in the hydrogen form (as indicated by the prefix letter H) or they may be base exchanged or impregnated to contain ammonium or a metal cation complement. It is desirable to calcine the zeolite after base exchange. The metal cations that may be present include any of the cations of the metals of Groups I through VIII of the periodic table. However, in the case of Group IA metals, the cation content should in no case be so large as to substantially eliminate the activity of the zeolite for the catalysis being employed in the instant invention.

In addition to the foregoing materials, the zeolites employed herein may be composited with a porous matrix material, such as alumina, silica-alumina, silica-magnesia, silica-zirconia, silica-thoria, silica-berylia, silica-titania as well as ternary compositions, such as silica-alumina-thoria, silica-alumina-zirconia, silica-alumina-magnesia and silica-magnesia-zirconia. The matrix may be in the form of a cogel. The relative proportions of zeolite component and inorganic oxide gel matrix may vary widely with the zeolite content ranging from between about 1 to about 99 percent by weight and more usually in the range of about 5 to about 80 percent by weight of the composite.

The reaction of isobutylene and methanol in the presence of any of the foregoing catalysts to provide MTBE can be effected at reaction conditions which include an elevated temperature in the range of from about 50° C. to about 400° C., preferably, from about 125° C. to about 200° C., a pressure in the range of from about atmospheric to about 1,500 psig, preferably from about 25 psig to about 1,000 psig, and a mole ratio of methanol to isobutylene of from about 0.1:1 to about 10:1, preferably from about 0.5 to about 1:1. When utilizing superatmospheric pressures as one of the reaction conditions, the pressure can be provided by the autogenous pressure of isobutylene, methanol, or both, if in the gaseous state. However, if both of the starting materials are in liquid state, said superatmospheric pressures can be provided by the introduction of a substantially inert gas such as nitrogen into the reaction zone, the amount of pressure which is used being that which is sufficient to maintain a major portion of the reactants in the liquid phase.

The process of this invention can be effected in any suitable manner and can comprise either a batch or continuous type operation. For example, when a batch type operation is used, methanol and the catalyst are placed in an appropriate apparatus such as, for example, an autoclave of the rotating or mixing type. Thereafter isobutylene, alone or in admixture with minor amounts of other butenes and/or butanes, whether in gaseous or liquid form, is charged to the reactor which is thereafter heated to the desired operating temperature, the superatmospheric pressure being afforded by isobutylene if in gaseous form. Alternatively speaking, if the isobutylene feed is in liquid form and super-atmospheric pressures are desired, said pressure is provided for by the introduction of nitrogen into the reactor prior to heating to the desired temperature. After maintaining the reactor at the desired operating conditions for a residence time which may range from about 0.5 up to about 20 hours or more in duration, heating is discontinued and the reactor and contents thereof are allowed to return to room temperature. Any excess pressure which may still be present is discharged and the reaction mixture is recovered. The mixture, after being separated from the catalyst by conventional means such as filtration when the catalyst remains as a solid after the reaction, is then subjected to conventional means of separation which may include washing, drying, extraction, fractional distillation, fractional crystallization, etc. whereby MTBE is separated from any unreacted starting materials and/or side reaction products which may have formed and is recovered.

It is also within the scope of this invention to carry out the process in a continuous manner of operation. When this type of operation is employed, a quantity of catalyst composition is placed in an appropriate apparatus which is maintained at the proper operating conditions of temperature and pressure. The reactants are continuously charged to this reactor through separate lines, or if so desired, they may be admixed prior to entry into said reactor and charged thereto in a single stream. Upon completion of the desired residence time in the reactor, the reactor effluent is continuously withdrawn and subjected to separation means of the type hereinbefore set forth in greater detail whereby MTBE is separated and recovered, the unreacted starting materials being recycled to form a portion of the feed stock. The catalyst can be present in the reactor as a fixed bed with the reactants being passed therethrough either in a continuous or intermittent (trickle) liquid stream or as a gaseous stream. The catalyst can also be present as a moving, or fluidized, bed with the reactants passing either concurrently or countercurrently to each other through the reactor. Alternatively, the catalyst can be charged to the reactor as a slurry or in solution in one or both of the starting materials.

The amount of catalyst employed herein can vary widely and will depend to some extent upon the nature of the catalyst, the concentration of the reactants, the temperature and pressure conditions and similar factors as recognized by those skilled in the art. In general, mole ratios of active catalyst component to isobutylene of from about 1:10 to about 1:10,000, and preferably, 1:100 to about 1:500 can be used with good results.

EXAMPLES 1-27

In the following examples which are illustrative of the use of catalyst compositions both within and outside the scope of the present invention (the latter being included by way of comparison) catalyst, isobutylene and methanol in the amounts indicated in the table below were added to a shaken 70 ml capacity stainless steel reactor. The reactor was sealed, heated to the indicated temperature for about 8 hours with continuous shaking with autogenous pressure being maintained for this period. At the conclusion of the reaction period, the contents of the reactor were withdrawn therefrom and subjected to analysis. The other conditions under which the syntheses were carried out, and the results thereof, are set forth in the following table.

In these data, the calculation for the theoretical amount of MTBE which could be produced was based on an assumption that there were no other reactions of methanol. However, in some syntheses, it was apparent that there were reactions of methanol other than that leading to the production of MTBE. In those cases, no value for theoretical amount of MTBE is given.

| Example | Catalyst/ Amount (gm) | Reactants (ml) Butene(s)[1] | Reactants (ml) Methanol | Reaction Temperature (°C.) | Composition of Reaction Products (volatiles) Butene(s) | MTBE | Dimers | Methanol | Trimers | Selectivity % | MTBE × 100 / (MTBE + Methanol) Observed | Theoretical |
|---|---|---|---|---|---|---|---|---|---|---|---|---|
| 1 | $W_4O_{11}$ on $SiO_2$ 7.0 | 20 I | 20 | 150 | 0.2 | 37.4 | 2.1 | 60.3 | 0 | 94.6 | 38.3 | 47 |
| 2 | $W_4O_{11}$ on $SiO_2$ 7.0 | 20 I | 20 | 270 | 36.4 | 4.1 | 41 | 7.4 | 11 | 7.3 | — | — |
| 3 | $H_3PO_4$ on $SiO_2$ 25 cc on silica gel | 10 I | 10 | 150 | 13.4 | 20 | 58.2 | 2.3 | 7.1 | 23.4 | — | — |
| 4 | Phosphotungstic Acid 1.74 | 10 I | 10 | 150 | 15.5 | 8.1 | 45.1 | 1.8 | 29.4 | — | — | — |
| 5 | $BPO_4$[2] 4.3 | 10 I | 10 | 150 | 10.6 | 38.4 | .4 | 50 | .6 | 97.5 | 43 | 43 |
| 6 | Dowex 50[3] 3.4 | 10 I | 10 | 150 | 16.2 | 27 | 28 | 26.5 | 2.1 | 47 | 49 | 47 |
| 7 | Phospho-Molybdic Acid 1.7 | 10 I | 10 | 150 | 5.9 | 6.1 | 43.7 | .9 | 43.2 | — | — | — |
| 8 | $BPO_4$ | 9.6 I | 5.4 | 90 | 8.6 | .093 | .023 | 67.0 | 0 | 80 | 0.10 | 84 |
| 9 | Dowex 50, 3.4 | 9.6 I | 5.4 | 90 | 6.7 | 37.6 | .405 | 50.9 | .033 | 98.8 | 42.5 | 84 |
| 10 | ZSM-5 0.51 | 15 I | 10 | 150 | 15.3 | 55 | 0.95 | 20.3 | 8.4 | 85 | 73 | 71 |
| 11 | $BPO_4$ 1.4 | 10 I | 15 | 120 | — | 1.41 | .288 | 98.3 | 0 | 83 | 1.4 | 31 |
| 13 | $BPO_4$ 1.8 | 5 I 5 M | 15 | 150 | 11.5 | 18.82 | .031 | 69.6 | 0 | 99.8 | 21 | 16 |
| 14 | $BPO_4$ 1.7 | 10 I | 15 | 150 | 7.8 | 21.8 | trace | 70.4 | 0 | 100 | 23.6 | 31 |
| 15 | $BPO_4$ 1.5 | 10 M | 15 | 150 | 9.1 | .03[4] | .066 | 90.8 | 0 | 31 | .03[4] | 31[4] |
| 16 | ZSM-5 0.54 | 5 I 5 M | 15 | 150 | 9.51 | 31.21 | 0.24 | 49.7 | 9.36 | 76.5 | 38.6 | 31 |
| 17 | $BPO_4$ 1.1 | 10 B | 15 | 150 | 15.18[5] | .029[5] | .121 | 68.37 | 16.3 | .17 | —[6] | — |
| 18 | ZSM-5 0.38 | 10 B | 15 | 150 | 16.6[5] | .923[5] | .417 | 61.91 | 20.13 | 4.3 | — | — |
| 19 | $BPO_4$ 1.2 | 10 I | 15 | 200 | 13.0 | 24 | 0 | 63 | 0 | 100 | 27.6 | 31 |
| 20 | $BPO_4$ 1.0 | 10 M | 15 | 200 | 22.6 | 1.0[4] | .03 | 76.3 | .13 | 43 | 1.3[4] | 31[4] |
| 21 | $W_4O_{11}$ on $SiO_2$ | 10 | 15 | 150 | 27.3 | .35[4] | .98 | 71.3 | .054 | 25 | .49[4] | 31[4] |

-continued

| Example | Catalyst/ Amount (gm) | Reactants (ml) Butene(s)[1] | Reactants (ml) Methanol | Reaction Temperature (°C.) | Composition of Reaction Products (volatiles) Butene(s) | MTBE | Dimers | Methanol | Trimers | Selectivity % | MTBE × 100 / (MTBE + Methanol) Observed | MTBE × 100 / (MTBE + Methanol) Theoretical |
|---|---|---|---|---|---|---|---|---|---|---|---|---|
| 22 | $W_4O_{11}$ on $SiO_2$ 4.2 3.8 | 10 M I | 15 | 150 | 10.6 | 36.2 | .75 | 52.5 | 0 | 98 | 40.8 | 31 |
| 23 | $MoO_3$ 2.26 | 10 M | 15 | 150 | 16.9 | 0 | .032 | 83.0 | 0 | 0 | — | 31[4] |
| 24 | $MoO_3$ 2.4 | 10 I | 15 | 150 | 12.6 | 3.82 | .056 | 83.6 | 0 | 98.5 | 4.0 | 31 |
| 25 | $TiO_2$ 4.0 | 15 I | 5 | 175 | 4.6 | .036 | .741 | 94.7 | 0 | 4.6 | .04 | 41 |
| 26 | Silica-alumina 0.6 | 18 I | 5 | 150 | 7.6 | 11.8 | .39 | 80.2 | 0 | 97 | 12.8 | 100 |
| 27 | Zirconium-tungstate 3.7 | 23 I | 5 | 150 | 7.17 | 8.97 | .34 | 83.5 | 0 | 96 | 9.7 | 100 |

[1] I = isobutylene; M = cis, trans butene-2; B = butadiene.
[2] Phosphorus: boron mole ratio - 0.65 in all examples illustrating this catalyst.
[3] Styrene - divinylbenzene ion exchange resin (Dow Chemical Co.).
[4] Probably $CH_3CH(OCH_3)C_2H_5$ from butene-2.
[5] Polymer formed. The ether was not MTBE.
[6] Dash indicates an undetermined value.

As these data show, the examples illustrative of the present invention (with the exception of Example 2 which suggests that the reaction of isobutylene and methanol may be temperature sensitive in certain cases) resulted in comparitively high selectivities for MTBE and fairly good conversion levels of isobutylene.

What is claimed is:

1. A process for preparing methyl tertiary-butyl ether which comprises reacting isobutylene and methanol in the presence of a catalytically effective amount of at least one heterogeneous catalyst selected from the group consisting of boron phosphate and blue tungsten oxide at a temperature of from about 50° C. to about 400° C.

2. The process of claim 1 wherein the mole ratio of methanol to isobutylene is from about 0.1:1 to about 10:1.

3. The process of claim 1 wherein the mole ratio of methanol to isobutylene is from about 0.5 to about 1:1.

4. The process of claim 1 wherein the mole ratio of boron to phosphorus in the boron phosphate is from about 0.4 to about 1.4.

5. The process of claim 1 wherein the mole ratio of boron to phosphorus in the boron phosphate is from about 0.5 to about 0.7.

6. The process of claim 1 wherein the catalyst composition comprises boron phosphate and/or blue tungsten oxide supported upon in inert inorganic carrier.

7. The process of claim 1 wherein the carrier is selected from the group consisting of zinc spinel, alumina, silica, magnesia, titania, silica-alumina, alumina-magnesia, zirconia, pumice, kieselguhr, a clay, bauxite and charcoal.

8. The process of claim 1 wherein the reaction of isobutylene and methanol is carried out at a temperature of from about 125° C. to about 200° C.

9. The process of claim 1 wherein the reaction of isobutylene and methanol is carried out at a pressure of from about atmospheric to about 1,500 psig.

10. The process of claim 1 wherein the reaction of isobutylene and methanol is carried out at a pressure of from about 25 psig to about 1,000 psig.

11. The process of claim 1 wherein the mole ratio of catalyst to isobutylene is from about 1:10 to about 1:10,000.

12. The process of claim 1 wherein the mole ratio of catalyst to isobutylene is from about 1:100 to about 1:500.

* * * * *

UNITED STATES PATENT AND TRADEMARK OFFICE
CERTIFICATE OF CORRECTION

PATENT NO. : 4,418,219
DATED : November 29, 1983
INVENTOR(S) : Ronnie M. Hanes; and Orville D Frampton It is certified that error appears in the above-identified patent and that said Letters Patent are hereby corrected as shown below:

ON THE COVER PAGE

[75], "Prampton" should read as --Frampton--.

Signed and Sealed this

Thirtieth Day of July 1985

[SEAL]

Attest:

DONALD J. QUIGG

Attesting Officer     Acting Commissioner of Patents and Trademarks